United States Patent [19]

Hopponen et al.

[11] Patent Number: 5,556,879
[45] Date of Patent: Sep. 17, 1996

[54] AQUEOUS SPECTINOMYCIN BORATE SOLUTIONS

[75] Inventors: Raymond E. Hopponen, Fort Dodge, Iowa; Lowell R. Macy, Vermillion, S. Dak.

[73] Assignee: Rhone Merieux, Inc., Athens, Ga.

[21] Appl. No.: 369,629

[22] Filed: Mar. 1, 1995

[51] Int. Cl.$^6$ .................................................. A01N 43/32
[52] U.S. Cl. ........................... 514/452; 424/659; 549/361
[58] Field of Search ............................ 549/361; 514/452; 424/659

[56] References Cited

PUBLICATIONS

"The Chemistry of Actinospectacin", Wiley, P. F., Argoudelis, A. D., Hoeksma, H. J., J. Am. Chem. Soc. 85, 2652, (1963).

"Stereochemistry and Absolute Configuration of the Antibiotic Spectinomycin", Cochran, T. G., Abraham, D. J., J.C.S. Chem. Comm. 495, (1972).

Primary Examiner—James J. Seidleck
Assistant Examiner—Terressa Mosley
Attorney, Agent, or Firm—Curtis, Morris & Safford, P.C.

[57] ABSTRACT

Aqueous pharmaceutical compositions containing up to about 40% spectinomycin, prepared by the reaction of the ketone hydrate of spectinomycin with boric acid to form the boron compound, and with a base such as sodium hydroxide to form the stable salt of the compound.

10 Claims, No Drawings

AQUEOUS SPECTINOMYCIN BORATE SOLUTIONS

TECHNICAL FIELD

This invention relates to antibiotic compositions suitable for pharmaceutical use, and in particular to aqueous solutions and suspensions of the antibiotic spectinomycin.

BACKGROUND OF THE INVENTION

Spectinomycin (MW 332 daltons) is the common name for an aminocyclitol antibiotic having the formula decahydro-4α,7,9-trihydroxy-2-methyl-6,8-bis(methylamino)-4H-pyrano[2,3-b][1,4]benzo-dioxin-4-one, ($C_{14}H_{24}N_2O_7$), the structure of which is provided as Formula I below.

Spectinomycin functions as an antimicrobial, and in particular as an inhibitor of protein synthesis in the bacterial cell, having a site of action at the 30S ribosomal subunit. In humans, the compound has found particular application as an antimicrobial against *N. gonorrhoeae*. In veterinary and research applications, the compound has been found to be active in a variety of applications, including the treatment of diseases caused by infectious organisms susceptible to spectinomycin.

The compound can be isolated from the fermentation broth of the soil microbe *Streptomyces spectabilis*. Spectinomycin is available from Upjohn, under the brand name "Trobicin", in the form of a sterile powder for intramuscular injection. The powder is reconstituted with an accompanying sterile diluent (bacteriostatic water) prior to use, to achieve a final injectable suspension having a concentration of 400 mg/ml.

Sterile spectinomycin hydrochloride is said to exist in the form of the pentahydrated dihydrochloride salt. In its dihydrochloride pentahydrate form, the molecule is believed to exist as a ketone hydrate, rather than in the carbonyl form. Rigorous drying is necessary to remove the water and enable the infrared spectrum to display a ketone absorption band. See, for instance, *"The Chemistry of Actinospcctacin"*, Wiley, P. F., Argoudelis, A. D., Hoeksema, H., J. Am. Chem. Soc. 85, 2652, (1963) and *"Stereochemistry and Absolute Configuration of the Antibiotic Spectinomycin"*, Cochran, T. G., Abraham, D. J., Martin, L. L., J.C.S. Chem. Comm. 494, (1972).

When prepared for pharmaceutical applications in solution, rather than suspension form, such solutions are typically limited to spectinomycin concentrations of about 10% or less, by weight based on the weight of the solution. The maximum aqueous solubility of spectinomycin in the form of available salts such as the dihydrochloride is approximately 14% by weight.

The preferred concentration for veterinary use, however, can frequently be higher than 10%. As a result, the veterinarian often needs to use the compound in the form of an unstable suspension, thereby limiting its usefulness.

The ability to obtain more highly concentrated, stable aqueous compositions of spectinomycin would be of particular value to the veterinary professional.

SUMMARY OF THE INVENTION

The present invention provides a stable, high potency, aqueous spectinomycin composition comprising;

(a) spectinomycin, present at a concentration of between about 10% and about 40%, based on the weight of the composition, (b) boric acid, present in an amount at least equimolar to that of the spectinomycin and forming a boron compound of spectinomycin, and (c) a base, present in an amount at least equi molar to that of the boric acid and forming the salt of the boron compound, the composition being in the form of a solution having a pH of about pH 6 to about pH 9.

While not intending to be bound by theory, it appears that spectinomycin is stabilized in concentrated, solution form according to the following sequence of events. Formula I (spectinomycin) is hydrated to the ketone hydrate of spectinomycin form (Formula II). As the ketone hydrate (Formula II), it is reactive with boric acid at the 4,4α hydroxyl positions to form a 4,4α borate compound, which in turn will react with a base such as sodium hydroxide to form a stable salt (Formula III).

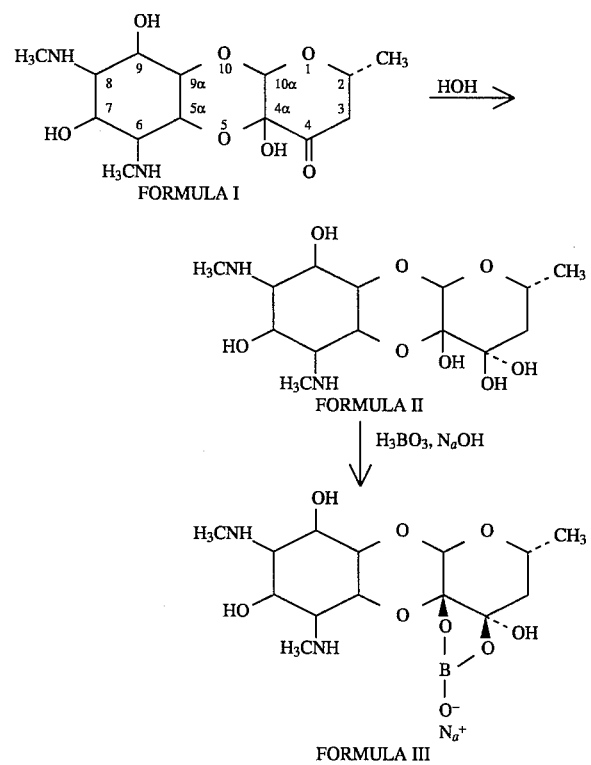

FORMULA I

FORMULA II

FORMULA III

"Spectinomycin", as used herein, refers to the above-described compound, as well as its antimicrobially active salts and analogues, in a form suitable to form a boron compound in the presence of boric acid. Preferably spectinomycin is provided in the form of the dihydrochloride pentahydrate, as described above. The term "boron compound of spectinomycin" will refer to the compound identified as decahydro-4,7,9-trihydroxy-2-methyl- 6,8-bis(methylamino)-4H-pyrano[2,3-b][1,4]benzodioxin-4,4α-borate ($C_{24}H_{26}N_2 BO_9$), the sodium salt of which is shown in Formula III above.

A preferred antibiotic concentration is in the range of about 10% to about 40%, and a particularly preferred concentration is in the range of about 20% to about 30%, and more preferably about 20% to about 40%, by weight, based on the weight of the final composition.

In another aspect, the invention provides a method of preparing a high potency, aqueous spectinomycin formulation, comprising the steps of:

(a) preparing an aqueous solution of boric acid;

(b) combining the boric acid solution with a desired amount of spectinomycin under conditions suitable to form the boron compound of spectinomycin; and (c) forming the salt of the boron compound by the addition of a substantially equimolar amount of a suitable base.

It has been found that high potency solutions of spectinomycin can be provided by means of a novel pharmaceutical composition comprising spectinomycin in the form of the salt of a boron compound of spectinomycin.

DETAILED DESCRIPTION

The present invention provides a stable, high potency aqueous formulation of spectinomycin in the form of a stabilized boron compound. Applicants have made unexpected use of the fact that spectinomycin, which is generally represented structurally as a ketone, is found to actually exist in the form of a ketone hydrate. The hydrate results in a structure having cis hydroxyl groups on adjacent carbon atoms.

Applicants have found that these hydroxyl groups offer a site at which boric acid can react to form a boron compound having strongly acidic properties and salt forming capabilities. The addition of an equimolar amount of a base such as sodium hydroxide leads to the formation of a highly water soluble salt. Solutions containing as much as 40% of spectinomycin can be prepared in this manner.

Spectinomycin, or its analogues, can be used in the form of any suitable pharmaceutically acceptable salt. Examples of suitable salts that can be used include such pharmaceutically acceptable salts as the hydrochloride, hydrobromide, sulfate, nitrate, ascorbate, citrate, gluconate, lactate, formate, glutamate, and the like. However, the preferred salt is the dihydrochloride pentahydrate.

Preferably, spectinomycin is provided at a final concentration of between about 10% and about 40% by weight, based on the weight of the final composition, with the boric acid and a suitable base present in substantially equimolar amounts. In particular, the boric acid is preferably used in a mole ratio of about 0.8 to about 1.3, and preferably about 0.9 to about 1.1, compared to the molar concentration of spectinomycin. Any suitable base, such as sodium hydroxide, can be used to form the salt form of the boron compound. The base is preferably used in a mole ratio of about 0.8 to about 1.3, and preferably about 0.9 to about 1.1, compared to the molar concentration of the boron compound. A composition of this invention can be readily prepared by mixing the components in any appropriate fashion. The addition of an equimolar amount of boric acid to a solution of a spectinomycin dihydrochloride pentahydrate results in a drop in pH as the boron compound is formed. For example, a spectinomycin solution containing 10% of spectinomycin as the dihydrochloride pentahydrate has a pH of 4.1. A boric acid solution containing an equimolar amount of boric acid has a pH of 4.5. A solution of a 10% spectinomycin as the dihydrochloride pentahydrate and an equimolar amount of boric acid has a pH of 2.5. These findings conform with the postulated reaction of boric acid with cis hydroxyl groups on adjacent carbon atoms.

A rigorously dried sample of spectinomycin dihydrochloride pentahydrate will exhibit the presence of a ketone group when subjected to infrared analysis. When subjected to similarly rigorous drying procedures, Applicants have found that neither the spectinomycin boron compound itself nor the sodium salt show the presence of a ketone group. These results provide further confirmation that the boric acid has reacted with the ketone hydrate group of the spectinomycin.

Even more surprisingly, solutions of the spectinomycin boron compound continue to demonstrate useful antimicrobial activity. In a preferred embodiment, the activity is substantially equal to the spectinomycin content. For example, solutions prepared to contain 10%, 20%, 30% and 40% of spectinomycin with equimolar amounts of boric acid and of sodium hydroxide demonstrate the expected level of antimicrobial activity.

Compositions of the present invention can be readily prepared by dissolving in water an amount of bode acid equimolar to the desired concentration of spectinomycin. A suitable salt of spectinomycin, e.g., in powder form, is added to the bode acid solution at a temperature of about 60° C. A suitable base, such as sodium hydroxide, is then added in an equimolar amount in order to form the sodium salt of the boron compound. The pH may be adjusted to a range of about 6 to 9.

Those skilled in the art will appreciate the manner in which the present composition can include conventional pharmaceutical adjuvants as well. For instance, a suitable antimicrobial agent, such as benzyl alcohol, can be added at a concentration of up to about 5% by weight, and preferably at a concentration of between about 1% to 2%. Likewise, suitable chemical preservatives can be included as well, such as sodium metabisulfite (0.5% to 1.0% by weight) or sodium formaldehyde sulfoxylate (0.1 to 0.5% by weight).

A composition of the present invention finds particular use as a parenteral or topical composition for human or veterinary use. The composition is easily syringable over a wide temperature range, and provides acceptable animal tissue tolerance as well as therapeutic blood levels.

The following Example is provided to illustrate, but not limit, the present invention.

EXAMPLE

One liter of a 20% solution of spectinomycin was prepared by adding the following ingredients.

| | |
|---|---|
| Spectinomycin dihydrochloride pentahydrate (based on potency of 605 micrograms per milligram) $\frac{200 \text{ g}}{0.605} = 330.6 \text{ g}$ | 330.6 g |
| Boric acid | 37.21 g |
| Sodium hydroxide (based on 100% purity, adjust for variance) | 24.08 g |
| Benzyl alcohol | 10.0 g |
| Sodium metabisulfite | 5.0 g |
| Water for injection qs to | 1000.0 mL |

The boric acid was dissolved in 700 ml of warm (60° C.) water. The spectinomycin was slowly added with stirring, after which the sodium hydroxide was added and dissolved. The benzyl alcohol and the sodium metabisulfite were then added with stirring. The final pH was adjusted to 6.2 with sodium hydroxide. The solution was cooled to room temperature and brought to volume with water.

The spectinomycin composition was found to be stable and provided the expected level of antimicrobial activity when assayed by a standard USP turbidometric procedure.

Stable and effective solutions of 30 and 40% spectinomycin were prepared as well. Since the borate compound is a strong acid, capable of forming esters with alcohols, both a liquid ethyl ester and a solid stearyl ester form have been prepared as well.

Both the spectinomycin boron compound and its sodium salt were separated from their solutions as solid materials. As expected, their melting points were different from that of spectinomycin dihydrochloride pentahydrate (m.p. 195°–196° C.). The boron compound melted at 204°–205° C., while the sodium salt of the compound did not melt below 240° C.

A weighed amount of the separated and dried sodium salt of the spectinomycin boron compound was re-dissolved in water. The resulting solution was assayed by atomic assay procedures for its sodium and boron content. The results corresponded to those predicted for the sodium salt of the boron compound of spectinomycin dihydrochloride pentahydrate. The predicted molecular weight of the salt-stabilized compound was also confirmed by sodium-boron assays. IR spectra comparisons of the spectinomycin boron compound, and its sodium salt, demonstrated the expected loss of the ketone functionality. Accordingly, Applicants have demonstrated that a stable, high potency composition of spectinomycin can be prepared and used in the manner presently described.

What is claimed is:

1. A stable, high potency aqueous spectinomycin composition comprising:

(a) spectinomycin, at a concentration of between about 10% and about 40% by weight, based on the weight of the composition, (b) boric acid, present in an amount at least equi molar to that of the spectinomycin and forming a boron compound of spectinomycin, and (c) a base, present in an amount at least equi molar to that of the boric acid and forming the salt of the boron compound, the composition being in the form of a solution having a pH of about pH 6 to about pH 9.

2. A composition according to claim 1, wherein the spectinomycin is in the form of the dihydrochloride pentahydrate.

3. A composition according to claim 1 wherein the composition is provided in the form of a sterile injectable composition.

4. A composition according to claim 1, wherein the spectinomycin is present in a concentration of between about 20% and about 30% by weight, based on the weight of the composition.

5. A stable, high potency aqueous spectinomycin composition comprising:

(a) spectinomycin, at a concentration of between about 10% and about 40% by weight, based on the weight of the composition, (b) boric acid, present in an amount about equimolar to that of the spectinomycin and forming a boron compound of spectinomycin, and (c) a base, present in an amount about equimolar to that of the boric acid and forming the salt of the boron compound, the composition being in the form of a solution having a pH of about pH 6 to about pH 9.

6. A composition according to claim 5, wherein the spectinomycin is in the form of the dihydrochloride pentahydrate.

7. A composition according to claim 5, wherein the composition is provided in the form of a sterile injectable composition.

8. A composition according to claim 5, wherein the spectinomycin is present in a concentration of between about 20% and about 30% by weight, based on the weight of the composition.

9. A composition according to claim 5, wherein the spectinomycin is present at a concentration of about 20%, the boric acid is present at a concentration of between 0.9 to 1.1 molar concentration, and the base is provided in the form of sodium hydroxide, present at between 0.9 and 1.1 molar concentration.

10. A method of preparing a stable, high potency, aqueous spectinomycin composition comprising the steps of:

(a) preparing an aqueous solution of boric acid at a concentration of between about 0.8 and 1.3 molar;

(b) combining the boric acid solution with spectinomycin in order to achieve a final concentration of between about 10% and about 40% by weight, under conditions suitable to form the boron compound; and (c) forming the salt of the boron compound by the addition of a base in an about equimolar amount, the composition being in the form of a solution having a pH of about pH 6 to about pH 9.

* * * * *

UNITED STATES PATENT AND TRADEMARK OFFICE
CERTIFICATE OF CORRECTION

PATENT NO. : 5,556,879
DATED : September 17, 1996
INVENTOR(S) : Hopponen et al.

It is certified that error appears in the above-indentified patent and that said Letters Patent is hereby corrected as shown below:

ON THE COVER PAGE: under item 21, please change " Appln. No. 369,629" to --Appln. No. 396,629--.

IN THE CLAIMS:
Column 5,
Claim 1, line 6: please change "equi molar" to --equimolar--.

Claim 1, line 9: please change "equi molar" to --equimolar--.

Signed and Sealed this

Sixth Day of January, 1998

*Attest:*

BRUCE LEHMAN

*Attesting Officer*          *Commissioner of Patents and Trademarks*